United States Patent [19]

Fehr et al.

[11] Patent Number: 5,602,311
[45] Date of Patent: Feb. 11, 1997

[54] SOYBEANS AND SOYBEANS PRODUCTS HAVING HIGH PALMITIC ACID CONTENT

[75] Inventors: Walter R. Fehr; Earl G. Hammond, both of Ames, Iowa

[73] Assignee: Iowa State University Research Foundation, Inc., Ames, Iowa

[21] Appl. No.: 376,466

[22] Filed: Jan. 20, 1995

Related U.S. Application Data

[63] Continuation of Ser. No. 180,114, Jan. 12, 1994, abandoned, which is a continuation of Ser. No. 839,328, Feb. 20, 1992, abandoned, which is a continuation-in-part of Ser. No. 461,341, Jan. 5, 1990, abandoned.

[51] Int. Cl.$^6$ .............................. A01H 5/00; A01H 5/10; C12N 15/01
[52] U.S. Cl. ................ 800/200; 800/230; 800/250; 800/DIG. 26; 800/DIG. 69; 435/172.1; 426/601
[58] Field of Search ...................... 800/200, 230, 800/250, DIG. 26, DIG. 69; 426/601; 435/172.1

[56] References Cited

PUBLICATIONS

Kuhr et al 1987 Release Notice for N85–2124, N85–2131 and N85–2176.
Carter et al 1988 Release Notice for C1726 and C1727.
Mounts et al 1987 In Soybean Improvement, Production and Uses; Agronomy Monograph No. 16; Wilcox (ed) pp. 819–845 and 860–865.
Neumunz 1978 J. Am. Oil Chem. Soc. 55: 396A–398A.
Weihrauch et al 1977 Food Technology 31:80–85 and 91.
Graef et al 1985 J. Am. Oil Chem Soc. 64:773–775.
Wilcox et al 1984 J Am Oil Chem Soc. 61:97–100.
Wilson et al 1981 Crop Sci 21:788–791.
Burton et al 1983 Crop Sci 23:744–747.
Erickson et al 1988 Crop Sci 28:644–646.
Bubeck et al 1989 (May–Jun.) Crop Sci 29:652–656.
Wilcox 1989 (5 Mar.) In Conf. Mundial de Investigation en Soja; pp. 28–39.

Primary Examiner—Patricia R. Moody
Attorney, Agent, or Firm—Burns, Doane, Swecker & Mathis, L.L.P.

[57] ABSTRACT

A method is described for producing soybean varieties and lines exhibiting palmitic acid contents of at least about 18.0% up to 30.0% or more. The novel soybean lines are obtained from a soybean seed designated A1937NMU-85 and its descendants, particular desirable progeny resulting from the cross of A1937NMU-85 with ElginEMS-421, and further with the cross of selected progeny with A89-259098.

14 Claims, No Drawings

5,602,311

SOYBEANS AND SOYBEANS PRODUCTS HAVING HIGH PALMITIC ACID CONTENT

This is a continuation of application Ser. No. 08/180,114, filed on 12 Jan. 1994 (now abandoned), which is a continuation of application Ser. No. 07/839,328, filed on 20 Feb. 1992 (now abandoned), which is a continuation-in-part of Ser. No. 07/461,341, filed 5 Jan. 1990 (now abandoned).

FIELD OF THE INVENTION

This invention relates to novel soybean seeds and products of soybean seeds, such as soybean oil, and, more particularly, to soybeans seeds and products characterized by extremely high levels of palmitic acid.

BACKGROUND OF THE INVENTION

Soybean seeds represent perhaps the most significant oilseed in the world. Soybean oil makes up approximately 28% of the world supply of fats and oils, has been considered to be the major vegetable oil produced and consumed in the United States, and more than 90% of the soybean oil is used in food products (World Soybean Research Conference III Proceeding, Shibles, R. (Ed.) 1985).

Soybeans thus represent a significant world-wide food source, providing an excellent source of protein. As such, soybeans represent potential alternatives to meats.

Tofu and soymilk are two principal food products derived from soybean seeds. More than one billion people in China and Southeast Asia, it has been stated, rely on tofu as a major food protein source. (Proc. Int. Soya Protein Food Conf., American Soybean Assoc., p. 35 (1970)). Soymilk is similarly an important source for food protein.

One application for which soybean oil may be used is the production of plastic fats (e.g.—shortenings and margarines). Such plastic fats are made with a matrix of solid fats whose interstices are filled with liquid oil. Solid fats can crystallize in several forms with different melting points and physical properties. The forms are commonly designated alpha, beta' and beta, with the beta form having the highest melting point and the greatest stability. Forms other than these three may also be present. The beta' form generally has the properties that are most usually desired in a plastic fat.

If the solid portion of the plastic fat contains about 15% or more of palmitic acid and the rest is stearic acid, it will stabilize in the beta' form. If the ratio of stearic/palmitic is higher, then the fat may convert to the beta form with its less desirable physical structure.

Soybean oil will most usually contain a level of about 10% palmitic acid or so. Accordingly, if such soybean oil is hydrogenated and made into a plastic fat, it will likely crystallize in the beta form. To prevent this, an oil such as cottonseed or palm oil that is richer in palmitic acid is blended with the soybean oil.

The use of either palm oil or cottonseed oil presents some difficulties. Some users thus consider palm oil to be undesirable based upon perceived health considerations. On the other hand, cottonseed oil is generally available only in limited amounts at a higher price than that of soybean oil. It would accordingly be highly desirable to be able to provide soybean varieties having sufficiently elevated palmitic acid contents so that plastic fats can be produced such that such products will stabilize in the beta' form.

Further, some producers for some plastic fat applications believe that soybean oil having a palmitic acid content in the range of about 13% or 14% to about 16% or so is preferred. For such applications, it would be highly desirable to be able to provide soybean varieties having a sufficiently high level of palmitic acid to use for blending with soybean varieties having more conventional palmitic acid contents to provide the desired intermediate range of palmitic acid content.

The palmitic acid levels in soybean seed oil range from 9.3% to 17.4% within the world collection (Erickson et al., *Journal of Heredity*, 79, p. 465, 1988). The Erickson et al. article reports the inheritance of altered palmitic acid percentages in two soybean mutants, C1726 and C1727. The level of palmitic acid in C1727 reported averages 17.3% palmitic acid in comparison to 11.5% in the oil of the parent cultivar "Century."

Despite the clear need for soybeans having a level of palmitic acid above that present in the world collection at the present time, this objective still remains to be achieved.

SUMMARY OF THE INVENTION

It has been discovered that a mutant line obtained from the parent variety Asgrow A1937 provides a population of soybean seeds exhibiting high levels of palmitic acid. The palmitic acid concentration capable of being obtained is about 18% of the total fatty acid present, even up to 20% or more.

Further, it has been discovered that crossing the Asgrow A1937 mutant with a second mutant provides a population of soybean seeds exhibiting significantly higher levels of palmitic acid than have been capable of being achieved. More particularly, soybean seeds having palmitic acid contents above about 20%, and, more preferably, of at least about 25% or more, have been achieved. Still further, it has been discovered that soybean seeds having palmitic acid contents of 30.0% or more may be obtained by crossing selected progeny with line A89-259098.

If desired, the soybeans of the present invention can be used as a donor parent in a backcrossing program with any desired commercial cultivar as a recurrent parent to isolate a commercial variety having desirable seed yield and other agronomic characteristics in addition to the high level of palmitic acid.

DETAILED DESCRIPTION OF PREFERRED EMBODIMENT

According to one aspect of the present invention, the novel soybean seeds and plants characterized by palmitic acid contents of at least 18% were obtained by preparation of a mutant line developed by treating the cultivar Asgrow A1937 with nitroso methyl urea (NMU). The mutation procedure utilized will be described in detail hereinafter in the Examples. The mutant line has been designated A1937NMU-85.

Pursuant to a further aspect of the present invention, crossing of the parent mutant line A1937NMU-85 with a second mutant line, ElginEMS-421, has been found to provide a population of soybean seeds with palmitic acid contents significantly above that of the parent line Asgrow A1937. The preparation of the mutant line, ElginEMS-421, will be described in conjunction with the Examples.

Crossing of the parent mutant lines A1937NMU-85 and ElginEMS-421 to obtain the soybean lines of the present invention can be carried out by any desired hybrid formation technique. Standard hybridization techniques are, of course, well known and may be utilized. As an illustrative example, hybridization techniques are disclosed in Fehr, *Principles of Cultivar Development*, Vol. 1, Theory and Technique, Chapter 13, pp. 156–164, Macmillan Publishing Company, New York, 1987, which hybridization techniques are herein incorporated by reference.

Progeny from the crossing of A1937NMU-85 and ElginEMS-421 yielded soybean seeds wherein the palmitic acid content is greater than 18%, preferably greater than about 20%, and more preferably, greater than about 25%.

The fatty acid composition was determined by gas-liquid chromatography using the method as generally outlined in Graef et al. (*Crop Sci.*, 25:1076–1079, 1985). Thus, in general, the method comprises (1) crushing the seed sample, (2) putting the crushed sample into a test tube with a hexane solvent and extracting the oil into the hexane, (3) the fatty acids in the oil are converted to their methyl esters using sodium methoxide and methanol, (4) water is added to inactivate the sodium methoxide catalyst, and (5) the methyl esters, which float to the top of the water layer, are diluted with hexane and become the sample that is introduced into the column of the gas chromatography apparatus.

As may be appreciated, this general methodology may be employed and specific aspects changed to lessen the time needed as desired. For example, the stationary phase selected for the columns will dictate the temperature at which the sample can be introduced.

None of the specifics utilized, e.g.—capillary versus packed columns, are considered to affect to any appreciable extent the results obtained for an analysis. Rather, such specifics affect the time required for sample preparation and analysis.

The percentages of the fatty acids set forth herein, unless otherwise designated, thus are on a weight basis and refer to the percentage of the methyl ester of palmitic acid or other fatty acid compared to the total methyl esters of the fatty acid composition in the sample being analyzed. This can also be taken as the weight percentage of the fatty acid itself because the difference between the palmitic acid content and that of its methyl ester as determined in the gas chromatography technique described herein is so minimal as may be ignored, as is commonly done in this field.

The gas chromatography techniques described herein are routinely used for analysis of the fatty acid composition of soybeans. The experimental error is considered to be within the range of from about 1 to 5% or so, depending upon the magnitude of the peak. For example, with a relatively large peak indicative of an oleic acid content of 50% or so, the experimental error may be as low as about 1% of the value, viz.—50±0.5%. At the other extreme, a small peak indicative of a stearic acid content of 4.0% may have an experimental error of about 5.0% of the value, viz.—4.0% ±0.2. A palmitic acid content of about 20% lies in the middle, with the expected error being about 2–3% of the reported value, viz.—20%±0.4 or 0.6%.

As may be appreciated, the palmitic acid levels of the soybeans of the present invention set forth herein were obtained from soybeans grown in Iowa and Puerto Rico. Growth under climatic conditions cooler or warmer may result in a somewhat altered fatty acid composition. However, while the specific results may vary somewhat depending upon the specific growing conditions experienced, the progeny of the present invention will be characterized by extremely high palmitic acid contents relative to other soybean lines grown under similar conditions.

Progeny exhibiting the desired high palmitic acid trait can be crossed with other progeny to provide a population of soybean seeds having extremely high palmitic acid contents. It can be expected that crosses utilizing the more desirable progeny should be capable of providing lines having palmitic acid contents up to about 30.0% or so.

Indeed, soybean lines having palmitic acid contents of 30.0% or more have been obtained by crossing selected progeny with line A89-259098. Parent line A89-259098 is described in our copending application, Ser. No. 07/643,277, the disclosure of said line being herein incorporated by reference. It can thus be expected that crosses utilizing the more desirable progeny should be capable of providing lines having palmitic acid contents up to about 35.0% or so.

Further, progeny can be crossed, if desired, with other progeny, or with any other soybean line or cultivar to yield a soybean cultivar having the desired seed yield or other desired agronomic traits as well as the desired high palmitic acid trait. Self-pollination of selected progeny may likewise yield lines having characteristics desired for some applications.

Any hybridization technique may be used, and many are known as has been described herein. For example, the selection of progeny having the desired high palmitic acid trait can be obtained by conducting backcrossing with a commercial variety until a desirable commercial variety has been isolated. Backcrossing techniques are known, as disclosed in Fehr, *Principles of Cultivar Development*, Vol. 1, Theory and Technique, Chapter 28, pp. 360–376, the disclosure of which is herein incorporated by reference.

As one example, backcrossing using the desired $F_2$ seeds obtained by natural self-pollination of the $F_1$ plants could be carried out as follows:

(1) Plant $F_1$ seeds obtained by crossing a parent with the desired high palmitic acid trait to the desired commercial cultivar (recurrent parent). Sample $F_2$ seeds from $F_1$ plants are analyzed for fatty acid concentration, and seeds with the desired high palmitic acid content are planted for backcrossing.

(2) Cross-pollinate the desired commercial cultivar (recurrent parent) with an $F_2$ plant having the high palmitic acid content.

(3) Plant the $BC_1F_1$ seeds and obtain $BC_1F_2$ seeds by natural self-pollination. Sample $BC_1F_2$ seeds are analyzed for fatty acid concentration, and those displaying the high palmitic acid trait are backcrossed to the recurrent parent.

(4) The backcross and selection procedure herein described (Step 3) can be repeated until lines with the desired high palmitic acid composition and agronomic performance are recovered. It is believed that four of these backcross cycles should serve to transfer the high palmitic acid trait to the desired cultivar (viz.—recurrent parent), although the number of such cycles can be fewer, or more, as is desired. The result is the production of a soybean line quite similar to the commercial cultivar except having the desired high palmitic acid content.

Any commercial cultivar (recurrent parent) desired may be employed for backcrossing. Factors such as, for example, seed yield, geographical area, and many others, as is known, will generally dictate the cultivar selected from the several hundred commercial cultivars available.

The following Examples are illustrative, but not in limitation, of the present invention. The gas chromatography results obtained from the instrument itself are reported to two decimal points (i.e.—"0.00"). As reported herein, the fatty acid values are set forth to one decimal point. Values of 6 or more in the second decimal point were raised (e.g.— 4.29 is reported herein as 4.3), values of 4 or less are ignored (e.g. —4.24 is reported as 4.2), values of 5 are raised if the first decimal is odd (e.g.—4.15 is reported as 4.2) and ignored if even e.g.—4.25 is reported as 4.2).

EXAMPLE 1

This Example describes the preparation of the mutant line A1937NMU-85.

Mutant line A1937NMU-85 was obtained from nitroso methyl urea (NMU) treatment of the parent variety Asgrow A1937. In May, 1985, 2,500 seeds of A1937 were soaked in 2.5 L distilled water in a 6 L flask for 9 hours at room temperature. The flask was aerated for the 9 hours of soaking. The water was drained from the flask, and 2.5 L of 2.5 mM NMU in 0.1 molar ["M"] phosphate buffer at pH 5.5 were added. The seeds were soaked with aeration for 3 hours, the solution was drained and the seeds were rinsed twice with distilled water. Treated seeds were placed in containers to prevent drying and transported to the Agricultural Engineering and Agronomy Research Center near Ames, Iowa. The seeds were planted 2.5 cm deep in moist soil within 4 hours after the last rinse. The soil was watered regularly to keep it moist until seeding emergence. The properties of the mutant seed and their progeny were evaluated beginning with the $M_4$ generation.

A similar number of seeds was harvested from each of the $M_1$ (first mutant generation) plants in the population to obtain 2,000 $M_2$ seeds. A random sample of 1,000 of the second generation $M_2$ seeds from the population was planted in October at the Iowa State University-University of Puerto Rico soybean nursery at Isabela, Puerto Rico. About 2,000 $M_3$ seeds were obtained by harvesting a similar number of seeds from each $M_2$ plant. In February, 1,000 $M_3$ seeds were planted in Puerto Rico. About 2,000 $M_4$ seeds were obtained by harvesting a similar number of seeds from each $M_3$ plant. In May, 1,000 $M_4$ seeds were planted at Ames. Five hundred $M_4$ plants were harvested individually from the population, and a 10-seed sample from selected plants was analyzed by gas-liquid chromatography to determine the fatty acid composition. $M_5$ progeny of selected plants were planted in Puerto Rico in February, 1987; and the results confirmed the unique fatty acid composition of the $M_4$ parent plant.

A 10-seed sample of the $M_4$ plant from which A1937NMU-85 originated and its parent was analyzed by gas-liquid chromatography, and the results are set forth in Table I:

TABLE I

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| A1937NMU-85 | 19.8 | 3.6 | 17.4 | 51.3 | 7.7 |
| A1937 Parent | 12.3 | 3.8 | 18.7 | 57.2 | 8.0 |

$M_5$ Progeny from the M4 plant A1937NMU-85 and the A1937 parent were analyzed by gas-liquid chromatography, and the results are set forth in Table II:

TABLE II

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| A1937NMU-85 | 20.1 | 3.8 | 18.5 | 49.9 | 7.6 |
| A1937 Parent | 12.1 | 4.6 | 27.1 | 50.1 | 6.1 |

Seeds of the soybean parent A1937NMU-85 have been deposited under the terms of the Budapest Treaty at the American Type Culture Collection (ATCC) at 12301 Parklawn Drive, Rockville, Md. 20852, U.S.A. More specifically 2,500 seeds of A1937NMU-85 were deposited on Jun. 18, 1996 and have been assigned ATCC Accession No. 97618.

EXAMPLE 2

This Example describes the preparation of the mutant line ElginEMS-421.

Mutant line ElginEMS-421 was obtained from ethyl methane sulfonate (EMS) treatment of the parent variety Elgin. In May, 1984, 2,500 seeds of Elgin were soaked in 2.5 L distilled water in a 6 L flask for 9 hours at room temperature. The flask was aerated for the 9 hours of soaking. The water was drained from the flask, and 2.5 L of 0.025 molar EMS in 0.1M phosphate buffer at pH 7 were added. The seeds were soaked for 9 hours, the solution was drained and the seeds were rinsed twice with distilled water. Treated seeds were placed in containers to prevent drying and transported to the Agricultural Engineering and Agronomy Research Center near Ames, Iowa. The seeds were planted 2.5 cm deep in moist soil within 4 hours after the last rinse. The soil was watered regularly to keep it moist until seedling emergence. The properties of the mutant seed and their progeny were evaluated beginning with the $M_2$ generation.

A similar number of seeds was harvested from each of the $M_1$ (first mutant generation) plants in a population to obtain 2,000 $M_2$ seeds for each population. A random sample of 1,000 of the second generation $M_2$ seeds from the population was planted in February at the Iowa State University-University of Puerto Rico Soybean nursery at Isabela, Puerto Rico. Five hundred $M_2$ plants were harvested individually from the population, and a 10-seed sample from selected plants was analyzed by gas-liquid chromatography to determine the fatty acid composition. $M_3$ progeny of the mutant plant were planted in Puerto Rico in November, 1986, and the results confirmed the unique fatty acid composition of the $M_2$ parent plant.

Table III sets forth the analysis of the 10-seed sample of the $M_2$ plant from which ElginEMS-421 originated as well as that of its parent:

TABLE III

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| ElginEMS-421 | 17.9 | 3.9 | 18.6 | 50.8 | 8.9 |
| Elgin Parent | 12.1 | 4.4 | 18.7 | 56.0 | 8.8 |

Table IV sets forth the analysis of $M_3$ progeny from the $M_2$ plant ElginEMS-421 and that of its parent:

TABLE IV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| ElginEMS-421 | 16.9 | 4.1 | 16.8 | 50.2 | 11.9 |
| Elgin Parent | 11.6 | 4.2 | 17.8 | 55.5 | 10.9 |

Seeds of the soybean parent Elgin EMS-421 have been deposited under the terms of the Budapest Treaty at the American Type Culture Collection (ATCC) at 12301 Parklawn Drive, Rockville, Md. 20852, U.S.A. More specifically 2,500 seeds of Elgin EMS-421 were deposited on Jun. 18, 1996 and have been assigned ATCC Accession No. 97617.

EXAMPLE 3

This Example describes the crossing of A1937NMU-85 and ElginEMS-421 to obtain the soybean lines of the present invention characterized by high palmitic acid contents.

Crosses were made between individual plants of A1937NMU-85 and ElginEMS-421 at the Agricultural Engineering and Agronomy Research Center near Ames, Iowa, in the summer of 1987. The hybrid $F_1$ seeds obtained from the different plant-to-plant crosses were kept separate, and were designated AX4659 through AX4663 and AX4676.

The $F_1$ seed was planted in the Iowa State University-University of Puerto Rico nursery at Isabela, Puerto Rico, in October, 1987. $F_2$ seeds were obtained by natural self-pollination. Each $F_1$ plant was harvested individually, and the $F_2$ seeds of each were maintained as a separate subpopulation.

Forty $F_2$ seeds from each of the six crosses were planted in Puerto Rico in February, 1988. $F_3$ seeds were obtained by natural self-pollination. $F_2$ plants were harvested individually. A 5-seed sample from each $F_2$ plant was analyzed for fatty acid composition by gas chromatography.

Table V summarizes the analysis of the fatty acid composition of the $F_3$ seeds from individual $F_2$ plants:

TABLE V

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4659-2-3 | 21.3 | 4.1 | 15.9 | 50.4 | 8.2 |
| AX4659-3-7 | 25.9 | 3.7 | 14.2 | 47.9 | 8.3 |
| AX4659-3-8 | 23.9 | 3.7 | 17.5 | 46.6 | 8.2 |
| AX4660-3-4 | 26.1 | 4.5 | 16.2 | 44.9 | 8.3 |
| AX4663-5-2 | 25.9 | 4.4 | 17.7 | 44.4 | 7.5 |
| AX4663-5-4 | 26.8 | 4.1 | 12.5 | 48.2 | 8.3 |
| AX4676-2-11 | 23.6 | 3.6 | 15.7 | 48.7 | 8.4 |
| A1937NMU-85 | 19.0 | 3.8 | 15.7 | 53.2 | 8.2 |
| ElginEMS-421 | 17.4 | 4.0 | 14.6 | 53.0 | 10.9 |

Twelve $F_3$ seeds from each selected $F_2$ plant were planted in the Iowa State University-University of Puerto Rico nursery in October, 1988. $F_4$ seeds were obtained by natural self-pollination. Each $F_3$ plant was harvested individually. A 10-seed sample from each $F_3$ plant was analyzed for fatty acid composition by gas chromatography.

Table VI summarizes the analysis of the fatty acid composition of the $F_4$ seeds from individual $F_3$ plants:

TABLE VI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4659-2-3-9 | 27.8 | 3.8 | 13.9 | 44.1 | 10.3 |
| AX4659-3-7-7 | 27.4 | 3.5 | 15.1 | 44.4 | 9.6 |
| AX4659-3-8-6 | 27.4 | 3.4 | 16.1 | 42.8 | 10.3 |
| AX4660-3-4-4 | 27.7 | 3.8 | 15.6 | 43.2 | 9.7 |
| AX4663-5-2-9 | 28.0 | 3.9 | 13.1 | 43.0 | 12.0 |
| AX4663-5-4-5 | 28.3 | 4.0 | 12.4 | 43.8 | 11.5 |
| AX4676-2-11-8 | 28.2 | 3.7 | 12.1 | 44.3 | 11.7 |
| A1937NMU-85 | 19.6 | 3.9 | 17.5 | 50.1 | 8.9 |
| ElginEMS-421 | 16.6 | 4.0 | 19.8 | 49.0 | 10.6 |

Thirty $F_4$ seeds from each selected $F_3$ plant were planted at the Agricultural Engineering and Agronomy Research Center near Ames, Iowa, in May, 1989. $F_5$ seeds were obtained by natural self-pollination. Each $F_4$ plant was harvested individually. A 5-seed sample from each of 10 $F_4$ plants tracing to an $F_3$ plant were analyzed for fatty acid composition by gas chromatography.

Table VII summarizes the analysis of the fatty acid composition of the $F_5$ seeds from individual $F_4$ plants, the parents, and C1727:

TABLE VII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4659-2-3-9 | 25.7 | 3.8 | 14.6 | 46.2 | 9.6 |
| AX4659-3-7-7 | 26.1 | 3.9 | 14.0 | 45.2 | 10.7 |
| AX4659-3-8-6 | 25.0 | 4.5 | 20.4 | 42.1 | 7.9 |
| AX4660-3-4-4 | 26.6 | 4.0 | 15.1 | 44.6 | 9.6 |
| AX4663-5-2-9 | 26.4 | 4.1 | 15.7 | 43.0 | 10.7 |
| AX4663-5-4-5 | 25.6 | 4.2 | 16.6 | 44.0 | 9.6 |
| AX4676-2-11-8 | 25.2 | 4.0 | 17.4 | 44.3 | 9.1 |
| A1937NMU-85 | 18.8 | 5.0 | 20.7 | 48.3 | 7.2 |
| ElginEMS-421 | 15.7 | 4.1 | 19.7 | 50.7 | 9.8 |
| C1727 | 15.6 | 3.6 | 19.2 | 53.2 | 8.4 |

EXAMPLE 4

This Example describes the crossing of AX4663-5-4-5 with A89-259098, a high stearic acid line, to obtain a soybean line according to the present invention characterized by an exceptionally high palmitic acid content.

Parent line AX4663-5-4-5 was obtained as described in Example 3. Parent line A89-259098 was obtained as described in our copending application, Ser. No. 07/643,277. The hybrid $F_1$ seeds obtained from the cross were designated AX7016-AX7019.

$F_1$ seeds of the cross were planted in February, 1990, in the Iowa State University-University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

Four individual $F_2$ seeds from each $F_1$ plant were split so that the embryonic axis was left intact. The portion without the embryonic axis (approximately one-third of the seed) was analyzed for fatty acid composition by gas chromatography.

Table VIII summarizes the analysis of the fatty acid composition of an F₂ seed having the desired high palmitic acid content and that of the parent lines:

TABLE VIII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX7017-1-3 | 30.4 | 5.2 | 10.1 | 42.6 | 11.7 |
| AX4663-5-4-5 | 28.6 | 4.0 | 11.9 | 43.0 | 12.4 |
| A89-259098 | 8.0 | 30.3 | 21.5 | 34.6 | 5.6 |

What is claimed is:

1. A method for producing a soybean plant that yields mature seed having an elevated endogenous palmitic acid content comprising:
   (a) crossing a first soybean parent plant that is A1937NMU-85 having ATCC Accession No. 97618, with a second soybean parent plant that is Elgin EMS-421 having ATFCC Accession No. 97617;
   (b) obtaining hybrid soybean seeds from the cross and germinating said seeds to produce segregating populations of soybean plants that are allowed to self-pollinate; and
   (c) selecting a plant of step (b) that yields mature seed following self pollination having an endogenous palmitic acid content in the oil thereof in an amount higher than the palmitic acid of the parent plant of step (a) having the higher endogenous palmitic acid content when the parent plants and the offspring of the cross are grown under the same conditions, and wherein the elevated palmitic acid content of the selected offspring of the cross is a heritable trait.

2. A soybean plant which upon self pollination yields mature seed that exhibits an elevated palmitic acid content and is the product of crossing a first soybean parent that is A1937NMU-85 having ATCC Accession No. 97618, with a second soybean parent that is Elgin EMS-421 having ATCC Accession No. 97617, and wherein the soybean plant resulting from said cross yields mature seed that provides an endogenous oil comprising palmitic acid in an amount higher than the endogenous palmitic acid content of the parent having the higher palmitic acid content when the parents plants and the offspring of said cross are grown under the same conditions, and wherein the elevated palmitic acid content of the offspring of the cross is a heritable trait.

3. A mature soybean seed formed by the self pollination of the soybean plant according to claim 2 and the descendants thereof that retains said elevated palmitic acid content when grown under the same conditions.

4. A method according to claim 1 wherein said soybean plant that is selected in step (c) contains an endogenous palmitic acid content in the oil of the mature seed formed thereon of at least about 18% by weight as determined by gas chromatography.

5. A method according to claim 1 wherein said soybean plant that is selected in step (c) contains an endogenous palmitic acid content in the oil of the mature seed formed thereon of greater than about 20% by weight as determined by gas chromatography.

6. A method according to claim 1 wherein said soybean plant that is selected in step (c) contains an endogenous palmitic acid content in the oil of the mature seed formed thereon of greater than about 25% by weight as determined by gas chromatography.

7. A method according to claim 1 wherein said soybean plant that is selected in step (c) contains an endogenous palmitic acid content in the oil of the mature seed formed thereon of at least about 30% by weight as determined by gas chromatography.

8. A method according to claim 1 wherein said soybean plant that is selected in step (c) contains an endogenous palmitic acid content in the oil of the mature seed formed thereon from about 21% to about 30% by weight as determined by gas chromatography.

9. A mature soybean seed formed by the self pollination of the plant selected in step (c) of the method of claim 1 and descendants thereof which upon self pollination.

10. A mature soybean seed according to claim 3 that contains an endogenous palmitic acid content in the oil thereof of at least about 18% by weight as determined by gas chromatography.

11. A mature soybean seed according to claim 3 that contains an endogenous palmitic acid content in the oil thereof of greater than about 20% by weight as determined by gas chromatography.

12. A mature soybean seed according to claim 3 that contains an endogenous palmitic acid content in the oil thereof of greater than about 25% by weight as determined by gas chromatography.

13. A mature soybean seed according to claim 3 that contains an endogenous palmitic acid content in the oil thereof of at least about 30% by weight as determined by gas chromatography.

14. A mature soybean seed according to claim 3 that contains an endogenous palmitic acid content in the oil thereof from about 21% to about 30% by weight as determined by gas chromatography.

* * * * *

UNITED STATES PATENT AND TRADEMARK OFFICE
CERTIFICATE OF CORRECTION

PATENT NO. : 5,602,311
DATED : February 11, 1997
INVENTOR(S) : WALTER R. FEHR et al.

It is certified that error appears in the above-indentified patent and that said Letters Patent is hereby corrected as shown below:

On the title page and column 1, line 1

<u>IN THE TITLE</u> [54]:

Please delete "SOYBEANS", second occurrence, and insert --SOYBEAN--.

Signed and Sealed this

Third Day of June, 1997

Attest:

BRUCE LEHMAN

*Attesting Officer*     Commissioner of Patents and Trademarks